United States Patent [19]
Fox

[11] Patent Number: 6,018,094
[45] Date of Patent: Jan. 25, 2000

[54] IMPLANT AND INSERT ASSEMBLY FOR BONE AND USES THEREOF

[75] Inventor: William Casey Fox, Pipe Creek, Tex.

[73] Assignee: BioMedical Enterprises, Inc., San Antonio, Tex.

[21] Appl. No.: 08/939,983

[22] Filed: Sep. 30, 1997

Related U.S. Application Data

[63] Continuation of application No. PCT/US96/04350, Mar. 29, 1996.

[51] Int. Cl.[7] ........................................................ A61F 2/02
[52] U.S. Cl. ................................ 623/11; 623/16; 606/191
[58] Field of Search .................................. 623/11, 12, 16, 623/66; 606/191, 198, 130; 604/167, 169; 600/561, 461

[56] References Cited

U.S. PATENT DOCUMENTS

| | | |
|---|---|---|
| 2,485,531 | 10/1949 | Dzus et al. . |
| 3,298,372 | 1/1967 | Feinberg . |
| 3,579,831 | 5/1971 | Stevens . |
| 3,820,534 | 6/1974 | Kraus et al. . |
| 3,896,504 | 7/1975 | Fischer . |
| 3,964,470 | 6/1976 | Trombley . |
| 3,968,790 | 7/1976 | Fukada et al. . |
| 3,995,644 | 12/1976 | Parsons . |
| 4,330,891 | 5/1982 | Branemark et al. . |
| 4,438,773 | 3/1984 | Letterio . |
| 4,511,335 | 4/1985 | Tatum . |
| 4,681,103 | 7/1987 | Boner et al. . |
| 4,772,261 | 9/1988 | Von Hoff et al. . |
| 4,805,634 | 2/1989 | Ullrich et al. . |
| 4,809,694 | 3/1989 | Ferrara . |
| 4,820,097 | 4/1989 | Maeda et al. . |
| 4,870,957 | 10/1989 | Goble et al. . |
| 4,880,006 | 11/1989 | Albrektsson et al. . |
| 4,917,703 | 4/1990 | Albrektsson . |
| 4,936,851 | 6/1990 | Fox et al. . |
| 4,950,296 | 8/1990 | McIntyre . |
| 4,997,433 | 3/1991 | Goble et al. . |
| 5,013,313 | 5/1991 | Surer . |
| 5,062,851 | 11/1991 | Branemark . |
| 5,139,502 | 8/1992 | Berg et al. . |
| 5,385,553 | 1/1995 | Hart et al. . |
| 5,405,388 | 4/1995 | Fox . |
| 5,569,205 | 10/1996 | Hart et al. . |

FOREIGN PATENT DOCUMENTS

| | | |
|---|---|---|
| 71-658 | 2/1983 | European Pat. Off. . |
| 3509-417A | 9/1986 | Germany . |
| 17592 | of 1913 | United Kingdom . |
| 1 548 964 | 7/1979 | United Kingdom . |
| 2 105 197 | 3/1983 | United Kingdom . |
| WO 86/06265 | 11/1986 | WIPO . |
| WO 90/00412 | 1/1990 | WIPO . |
| WO 96/29953 | 10/1996 | WIPO . |

OTHER PUBLICATIONS

Albrektsson, et al., "Osscointegrated Titanium Implants," *Acta orthop. scand.* 52 155–170, 1981.

Albrektsson et al., "A Method for Short– and Long–term In Vivo Study of the Bone–Implant Interface," *Clinical Orthopaedics and Related Research*, No. 159, pp. 269–273, Sep. 1981.

(List continued on next page.)

*Primary Examiner*—David J. Isabella
*Attorney, Agent, or Firm*—Akin, Gump, Strauss, Hauer & Feld, L.L.P.

[57] ABSTRACT

An implant port for repeated access to the medullary portion of bone is provided. The implant port includes an access port fittable into a surgically constructed bone orifice and an insert means that seals and fills the port volume. A penetrable insert means allows repeated access within bone using sharp surgical instruments; while an adapter means allows guided placement of a surgical instrument, such as a catheter, optical device, or rotating cutter. Skeletal surgery from the inside of bone is contemplated using the implant port provided.

21 Claims, 7 Drawing Sheets

OTHER PUBLICATIONS

Aufdemorte, et al., "A Novel Orthopaedic Implant to Repeatedly Sample Cancellous Bone for Histomorphometric Analysis," *The 5th International Congress on Bone Morphometry,* Niigata, Japan, pp. 260–263, Jul. 1988.

Aufdemorte, et al., "An Intraosseous Device for Studies of Bone–Healing," *The Journal of Bone and Joint Surgery, Incorporated,* vol. 74–A, No. 8, pp. 1153–1161, Sep. 1992.

Drinker, et al., "The Circulation in the Mammalian Bone–Marrow," *The American Journal of Physiology,* vol. 62, No. 1, pp. 1–92, Sep. 1, 1922.

Fox, "*Osseous Implants for Experimental Studies of Bone Marrow, and Materials Biocompatibility*", May 1990, Dissertation Catalogued Sep. 1991.

Fox, et al., "Experience with Osseous Implants for Bone and Biomaterials Research," *Journal of Long–Term Effects of Medical Implants,* 3(1):1–27, 1993.

Fox, W., et al., "Osseous implant for studies of biomaterials using an in vivo electrochemical transducer," *Journal of Biomedical Materials Research,* vol. 27, 763–773, 1993.

Heinild, S., et al., "Bone Marrow Infusion in Childhood," *The Journal of Pediactrics,* 30:400–412, 1947.

Kälebo, P., et al., "Recurrent bone regeneration in titanium implants. Experimental model for determining the healing capacity of bone using quantitative microradiography," *Biomaterials,* 9(4):295–301, 1988.

Meola, F., "Bone Marrow Infusions As A Routine Procedure In Children," *The Journal of Pediactrics,* 25:13–16, 1949.

Papper, E., The Bone Marrow Route for Injecting Fluids And Drugs Into The General Circulation, *Anesthesiology,* vol. 3, pp. 307–313, May 1942.

Rosetti, V., et al., "Intraosseous Infusion: An Alternative Route of Pediatric Intravascular Access," *Annals of Emergency Medicine,* 14:9, pp. 103/885–106/888, Sep. 1985.

Shoor, P., et al., "Intraosseous Infusion: Pressure–flow Relationship and Pharmacokinetics," *The Journal of Trauma,* vol. 19, No. 10, pp. 772–774, Oct. 1979.

Tocantins, L., et al., "Infusions of Blood and Other Fluids Via The Bone Marrow in Traumatic Shock and Other Forms of Peripheral Circulatory Failure," *Annals of Surgery,* vol. 114, No. 6, pp. 1085–1092, Dec. 1941.

Valdes, M., "Intraosseous Fluid Administration In Emergencies," *The Lancet,* pp. 1235–1236, Jun. 11, 1977.

Wright, J., et al., "Electrolysis and Stainless Steel in Bone," *The Journal of Bone and Joint Surgery,* vol. 38B, No. 3, pp. 745–753, Aug. 1956.

BioMedical Enterprises, Inc., "Cancellous Access Port," Brochure, Sep. 2, 1992.

Kälebo, P., *On Experimental Bone Regeneration in Titanium Implants,* Göteborg 1987.

Albrektsson, T., et al., "The Harvest Chamber—A Newly Developed Implant for Analysis of Bone Remodeling In Situ," *Biomaterials and Biomechanics,* p. 283–288, 1983.

Kälebo, P., *Bone Formation Rate in Osseointegrated Titanium Implants,* Submitted for publication Feb. 1987.

Kälebo, P., et al., "Bone Healing Following Irradiation During Tourniquet Ischaemia," *Acta Oncologica,* 26:63–69; 1987.

Kälebo, P., "On Experimental Regeneration in Titanium Implants," pp. 1–17, 1987.

Kälebo, P., and K.G. Strid, "Bone Mass Determination from Microradiographs by Computer–Assisted Videodensitometry," pp. 1–15, 1987.

International Search Report mailed Aug. 19, 1996.

U.S. Serial No. 08/357,072 to Fox et al. filed Dec. 15, 1994.

U.S. Serial No. 08/413,603 to Fox filed Mar. 30, 1995.

IMPLANT AND INSERT ASSEMBLY FOR BONE AND USES THEREOF

This application is a continuation application of co-pending international application PCT/US96/04350 filed Mar. 29, 1996, incorporated by reference herein.

FIELD OF THE INVENTION

The present invention relates to bone implants and surgical devices, and to methods that include the surgical manipulation of bone, marrow and cartilage. In particular, the invention relates to an implant port that provides repeatable access to the medullary compartment of bone. Further, devices of the present invention allow surgery of bone from within the medullary compartment of bone.

BACKGROUND OF THE INVENTION

Bone implants have been used to solve healthcare problems of orthopedic and maxillofacial reconstruction, prosthesis and denture fixation, and fracture stabilization. Additionally, bone implants have been developed to advance the knowledge of bone healing and remodeling as well as the interaction of bone and implant material or devices.

The osseous infusion capability of an implant system builds on the use of long bones, especially the sternum, for acute access to the cardiovascular system. Later, tibial and sternal routes were used for access to the vascular system in children and adults. Historically, a wide range of fluids have been infused (blood, serum, saline, etc.). In a review of 4359 attempted infusions; 89 were complete failures, 27 incidences of osteomyelitis occurred, and 10 other complications were reported (Rosetti et al., *A Emer Med* 14.9;103–105, 1985).

U.S. Pat. No. 4,772,261 relates to an intramedullary catheter containing a tubular conduit portion and a head portion; the conduit is elongated and needle-like to define a passage. A seal mechanism is intermitted into a cavity in the head portion, the seal mechanism includes a silastic self-sealing membrane. U.S. Pat. No. 4,936,851 relates to an analytic bone implant for obtaining new bone growth for histologic and morphometric analysis. U.S. Pat. No. 4,880,006 relates to a bone ingrowth chamber for studying bone ingrowth in an implant in response to locally administered test substances of different types. The ability to obtain a biopsy of cortical bone or cancellous tissue following complete healing and mineralization of this tissue is severely compromised by the design of the chamber as set forth therein.

A cancellous access port biopsy apparatus, which is a three-component titanium alloy device consisting of a cap, tissue basket, and basket end plate, has been described (Fox, WC, "Osseous Implants for Experimental Studies of Bone, Marrow, and Materials Biocompatibility," Dissertation, The University of Texas at Austin, May 1991).

Deficiencies in prior art bone implants include: i) blockage due to dead space in conduits or cavities, ii) microbial colonization, iii) exfoliation of the implant, iv) difficulty in surgical placement, v) a prior art conduit is not fabricated from materials such as titanium that have an affinity for bone because, for example, titanium will conduct bone into the conduit and block infusion, vi) failures of the mechanism, vii) the inability to acquire a biopsy, and viii) the inability to replace a sealing means or clear the device without explantation. Explantation of the device generally damages the surrounding bone, leaving the site unsuitable for future use. Because these prior art devices and techniques are not completely satisfactory, the present inventor has searched for improvements and provides the invention described herein.

SUMMARY OF THE INVENTION

The present invention provides an implant port useful for minimally invasive surgical manipulation of bone. By "implant port" is meant a device that can be placed in bone temporarily or essentially permanently and provides a passage from the outside of bone into the inside of bone through which instruments may repeatedly pass for surgical manipulations. The implant port provides access to the medullary compartment of bone and comprises an access port and an insert means; the access port having an outer surface and an inner surface, the inner surface formed by a longitudinally oriented bore, a predetermined length terminating in a first end and a second end, a plurality of longitudinally oriented flutes that penetrate the outer surface and extend from the first end for a significant portion of the access port length, and a bead or plurality of beads on the outer surface adjacent to the first end. The insert means is means for inserting surgical assemblies, the means substantially filling the bore of the access port when positioned in the access port. The insert means may be a penetrable insert or an adapter insert.

The access port may have external means or internal means of insert fixation. The means of insert fixation are preferably selected from the group consisting of threads, press fits, and grooves. Biocompatible adhesives are another means of insert fixation. The bead or plurality of beads may have a sharp thread-like profile, a gently bulging contour, or a shape in between a sharp thread-like profile and a gently bulging contour. The function of the bead is to assist in holding the implant in place by being positioned on the medullary side of bone in a bone orifice; the bead resists any movement of the implant out of the bone orifice.

By "penetrable insert" is meant a solid plug-like insert that can be repeatedly penetrated by sharp instruments without substantial wear. Preferably, the penetrable insert contacts medullary bone tissue and overlying soft tissue during use. The penetrable insert may be formed from a non-osseous-integrating material such as, for example, a polymer selected from the group consisting of polyethylene, teflon and nylon. The non-osseous-integrating material may be a synthetic polymer, such as a silicone elastomer. A penetrable insert may comprise a guide port and a flapper valve, and further comprise a flapper strike plate. The guide port may be tapered in a further embodiment of a penetrable means. The implant port having a penetrable means may further comprise a cap, and the cap may have an insert access bore for access to a penetrable insert.

By "adapter insert" is meant an insert modified to allow passage of instruments into and out of the insert. In one embodiment, the adapter insert comprises a guide tube for directing a surgical instrument into the medullary compartment of bone. In another embodiment, the adapter insert is formed or molded to accommodate a swivel ball. In this embodiment, adapter insert and the swivel ball each have a bore into which a guide tube may be inserted by positioning the bore of the swivel ball in line with the bore of the adapter insert. The guide tube provides direction for an instrument inserted therein. When not in use, each bore may be filled with flexible wire, for example, and the swivel ball turned such that the passage is closed. In yet a further embodiment, the adapter insert is a bone biopsy assembly.

The implant port of the present invention, in a further embodiment, comprises a surgically-related instrument. By "surgically-related" is meant a surgical instrument or an instrument not normally used in surgery but is needed for a bone-related procedure. Examples of a surgically-related instrument include a needle, a catheter, an optical device, a manual or motor driven cutter, a suction instrument, or the like.

A method of using an implant port of the present invention in surgery of bone is an aspect of the invention. The method comprises the steps of i) preparing an orifice in bone, the orifice being in cortical bone and exposing the medullary portion, ii) placing an access port within the orifice, and iii) securing an insert means within the access port. Further, if the insert means is an adapter means, guide tubes may be inserted through the adapter means for guiding surgical instruments, or, if the insert means is a penetrable insert, surgical instruments may be inserted through the penetrable insert for surgical applications.

Surgery of bone means any procedure that manipulates bone, such as, for example, cutting medullary tissue, viewing or making measurements inside of bone, cauterizing medullary tissue, infusing fluids into bone for transport to limbic, extracellular or cardiovascular systems, or aspirating fluids from bone, for example. Surgery of bone includes manipulations made from within bone. With the use of the implant port of the present invention, a surgical instrument may be inserted through an implant port at a first site and used to perform surgery at a second site within the same bone. More than one implant port may be inserted into a bone if needed. Surgery of bone from within bone is advantageous in that bone lesions, fractures, or necrotic tissue of bone can be resected or treated without incision and retraction of the overlying soft-tissue and destruction of the vital blood supply. The ability to enter at a distant site and manipulate tissue from within without damaging the tissue overlying a diseased or injured site is helpful in assuring that a sufficient blood supply is available to support healing and in minimizing exposure of the site to contaminants. A method for surgery of bone from within bone is an aspect of the invention, the method comprises accessing bone by constructing an orifice, and inserting a surgically-related instrument through the orifice for manipulation or viewing at a site separate from the orifice. A surgically-related instrument is as herein defined.

The present invention contemplates use of an implant port of the present invention with an optical device for viewing bone or marrow tissue; with a catheter or a needle for delivering fluids into bone or for delivery of treatments having a solid physical form; with a suction instrument for aspirating fluids from bone; with a cutter, a suction instrument, a catheter or a needle for biopsy of bone; or the like.

The implant port allows collection of bone marrow and medullary tissue under sterile conditions for transplantation to another site in a patient. The aspirate may be processed aseptically, it may be concentrated, or it may be combined with donor or synthetic bone material for the treatment of bone at a distant skeletal site. This distant site might be accessed using another implant port of the present invention with an infusion catheter, for example.

A further aspect of the invention is the use of a bone tissue aspirate processing system that connects to the implant port, collects tissue, processes tissue and delivers it to a surgical site for the facilitation of healing of bone marrow transplantation. The bone tissue aspirate processing system may combine collected tissue with donor or synthetic bone replacement materials for transplantation.

Several significant advantages are achieved by the present invention.

1. The implant port is fabricated from a bone-conducting material, a bone-conducting material is a material that forms direct contact with living bone without interpositioned fibrous connective tissue. Such materials enhance the likelihood of long term fixation of the implant port into surrounding cortical bone due to direct contact and molecular adhesion with structurally strong bone.

2. When repeatedly penetrated by a needle for infusion or aspiration, for example, a penetrable insert means will fail. An advantage of the present implant port is that the insert means is replaceable using a procedure that is minimally invasive to bone.

3. Another advantage is that one implant port can accept a plurality of adapters, inserts and surgical instruments.

4. The lack of a requirement to place threads into the bone orifice eliminates any possibility that threads would be stripped during taping or insertion of the device.

5. The implant port of the present invention eliminates any conduit, cavity or possibility of implant blockage, and reduces the chance of microbial colonization, by contacting both medullary tissue and overlying soft-tissue. Having the penetrable insert means or adapter insert means contact or be in close proximity to the blood supply of bone eliminates any potential for bone to heal in or under the implant port. Such bone growth would separate the implant from the medullary vasculature or medullary space within bone and is not desirable.

A further aspect of the present invention is a bone insert assembly for access to the medullary compartment of bone. A bone insert assembly comprises an insert means for inserting a surgically-related instrument, and a surgically related instrument. In this embodiment, the assembly is held in place manually, for example, during surgery since the assembly lacks an access port or a means of fixation to bone tissue. The insert means may comprise a swivel ball or an adapter insert, a guide tube, or combinations thereof. Preferably, the surgically related instrument is a rotating cutter or an optical device. The bone insert assembly is contemplated for any of the uses cited above for the implant port, albeit temporarily for comparatively short procedures.

Following long-standing patent law convention, the terms "a" and "an" mean "one or more" when used in this application, including the claims.

BRIEF DESCRIPTION OF THE DRAWINGS

Further objects and advantages of this invention will become apparent from consideration of the drawings and ensuing description of the preferred embodiments.

Figure 1:
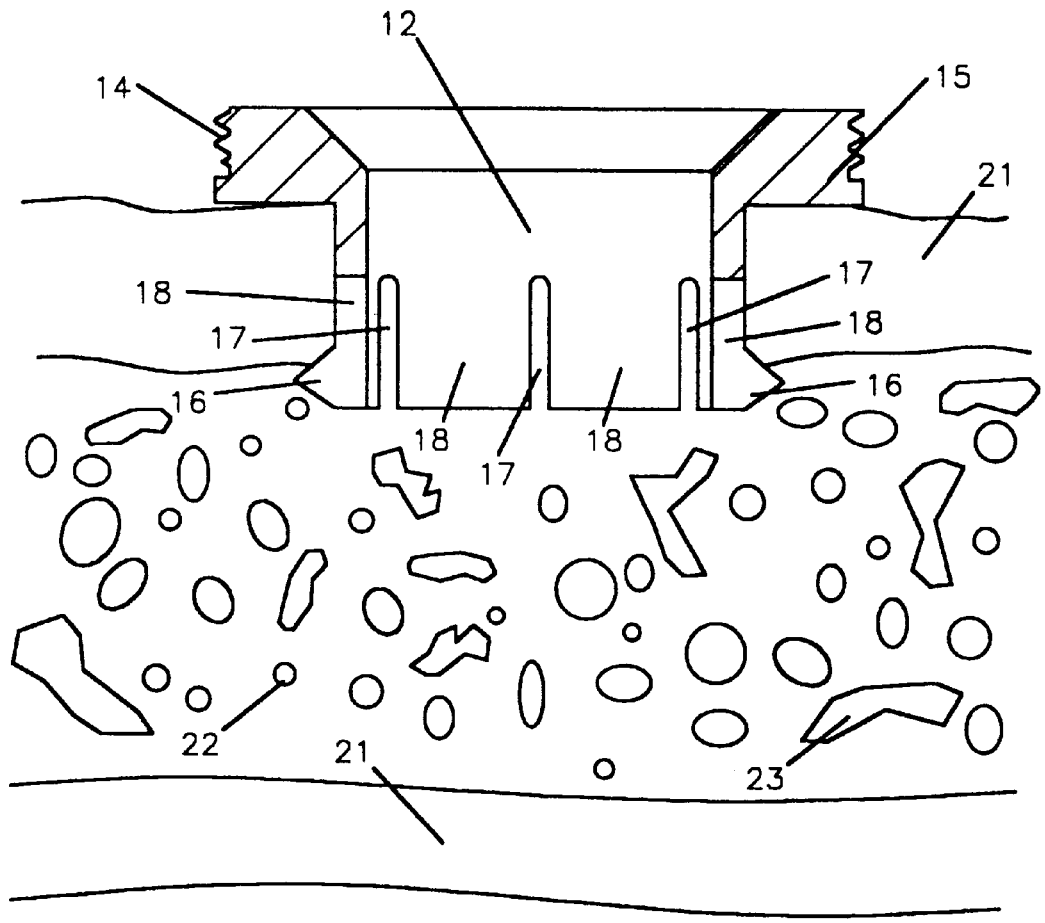
FIG. 1 is a cross-sectional plane view of an access port having external means of insert fixation in situ in bone.

LIST OF REFERENCE NUMERALS 12. bore
13. port with internal means of insert fixation
14. port seal ring retaining threads
15. port with external means of insert fixation
16. port anchor bead
17. port flutes
18. elastic prongs
19. penetrable bore insert
20. cap
21. cortical bone
22. marrow or bone cells
23. cancellous bone trabeculae
24. insert access bore
25. cap retaining threads
26. port bore adapter insert threads
27. bore adapter insert
28. guide tube
29. bore adapter insert threads
30. infusion or aspiration needle
31. fiber optic for illumination and observation
32. rotating cutter
33. aspiration catheter
34. needle flapper valve insert
35. needle guide port
36. flapper valve
37. flapper strike plate
40. swivel ball adapter insert
43. keeper ring
46. swivel ball
49. cutter drive shaft
52. grip

DETAILED DESCRIPTION OF THE PREFERRED EMBODIMENTS

The present invention provides an implant port for bone or hard tissue, such as cartilage, that includes an access port and either a penetrable insert means or an adapter insert means. The access port of the implant is placed in a surgically constructed orifice in bone tissue, and together with an insert means, acts as a port or portal into bone for numerous applications, such as the manipulation of marrow, bone, cartilage, or the like. The implant port is designed and constructed so as to eliminate any void that might tend to fill with tissue and block the use of the port.

Materials suitable for fabrication of an access port, adapter insert, or a swivel ball as described herein may be made out of a material that is at least biocompatible for the length of intended use, and has sufficient structural strength. Exemplary materials include. but are not limited to, titanium; a titanium alloy; stainless steel; a chromium cobalt alloy; silica glass; calcium phosphate; calcium carbonate; a silicone elastomer; a polymer such as delrin, nylon, polyester, polymethylmethacrylate, or polyethylene; or a ceramic such as alumina or silica glass.

Access port: An access port (15, 13) can be further described as having a first and a second end, an outer surface, and an inner bore (12) extending from the first end to the second end along a longitudinal axis. The bore (12) forms an opening into bone when the port is placed in a surgically constructed orifice in bone. The port also has a plurality of flutes (17) cut through the periphery parallel to the longitudinal axis of the bore that forms prongs (18). The port flutes (17) are cut with smooth edges to promote bone ingrowth and torsional resistance. The prongs (18) serve to resist port (15, 13) rotation; they also are flexible and pliant, yielding when the access port is pressed into or pulled from a cortical bone (21) orifice. This yielding action of the prongs (18), when press-fit into bone, allows the access port to be placed without the use of special tools to tap the bone defect. The access port is further externally grooved or beaded (16) circumferentially to resist forces tending to pull or push out the implant.

The access port resembles a plug that generally has a length less than its diameter. The access port is not in the form of an elongated conduit that can fill or become obstructed with tissue. The length of the access port is slightly greater than the thickness of the cortex of bone since the beads are designed to anchor the port just inside the cortex of bone.

Figure 3:
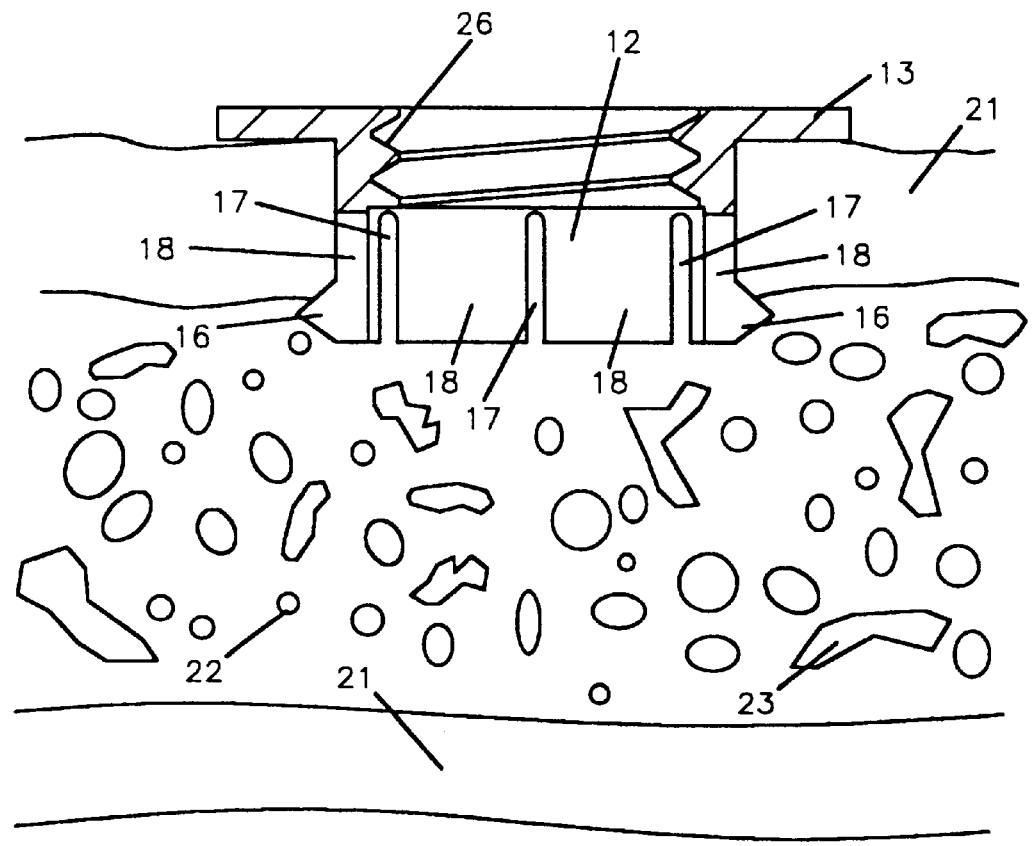
FIG. 3 is a cross-sectional plane view of an access port having internal means of insert fixation in situ in bone.

Embodiments of the access port of the present invention include an access port (13) having internal means of insert fixation as shown in FIG. 3, or an access port (15) having external means of insert fixation as shown in FIG. 1. Means of internal or external fixation of a penetrable insert or an adapter insert within an access port include, but are not limited to, threads, press-fit, grooves in the bore and beads on the insert, or use of a biocompatible adhesive, for example. The means of insert fixation allows placement of an insert directly to the access port (13) through the use of threads (26), or to the access port (15) through the use of a cap (20). The cap may have a bore (24) to access a penetrable means (19), and a means such as threads (25) to fasten the cap to the external aspect of the access port (15).

The access port has appropriate length to cause the first end to extend into the medullary portion of bone. The access port is provided in several lengths to accommodate individual variation in cortical bone (21) thickness. The access port should not reach so far into bone that it damages local medullary tissue and the cardiovascular system; the port should just maintain an opening into the medullary compartment of bone, thereby restricting cortical bone from healing and closing the access port. Access ports have been constructed of titanium alloy; exemplary sizes of ports that have been constructed have a diameter of about 5 mm, 8 mm, or 12 mm, and a length ranging from about 3 mm to 12 mm.

The implant port of the present invention includes a penetrable insert means or an adapter insert means, the means fitting into the access port. The penetrable insert means or the adapter insert means allow insertion of various surgically-related assemblies that support several modalities of medical treatment.

Penetrable insert means: A penetrable insert (19) may be a non-osseous-integrating plug or may be an elastomeric seal, for example. By "penetrable" means that the insert is made of material that may be penetrated or inserted into repeatedly by a tool such as a needle, for example, without substantially damaging the insert. The insert material is solid and sufficiently pliable that it substantially returns to its original shape after the tool has been removed. It is desirable that bone not heal or grow into the penetrable insert. Synthetic polymers are materials that will prevent healing of bone at the materials interface with bone. Therefore, a material such as, but not limited to, a silicone elastomer, polyethylene, and teflon are exemplary of materials that are non-osseous-integrating, are penetrable with a needle, for example, and are suitable as compositions for making penetrable means.

A penetrable insert (19) fills the bore of the access port from the fluted end at the medullary compartment of bone to the bone surface end at overlying soft-tissue space and seals to the access port. The assembled access port (15, 13) and penetrable insert (19) forms a self-sealing implant port that allows access into the medullary compartment of bone. The insert (19) impedes extravasation and allows the introduction of needles and instruments through the access port (15, 13) and into the medullary compartment of bone.

Figure 2:
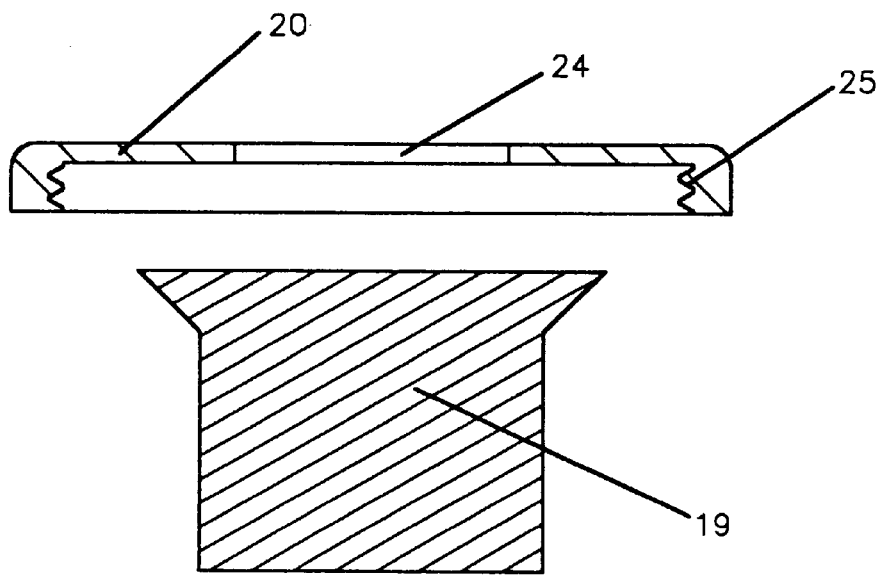
FIG. 2 is a cross-sectional plane view of a penetrable bore insert and a cap for insertion into and placement on the access port, respectively.
Figure 5:
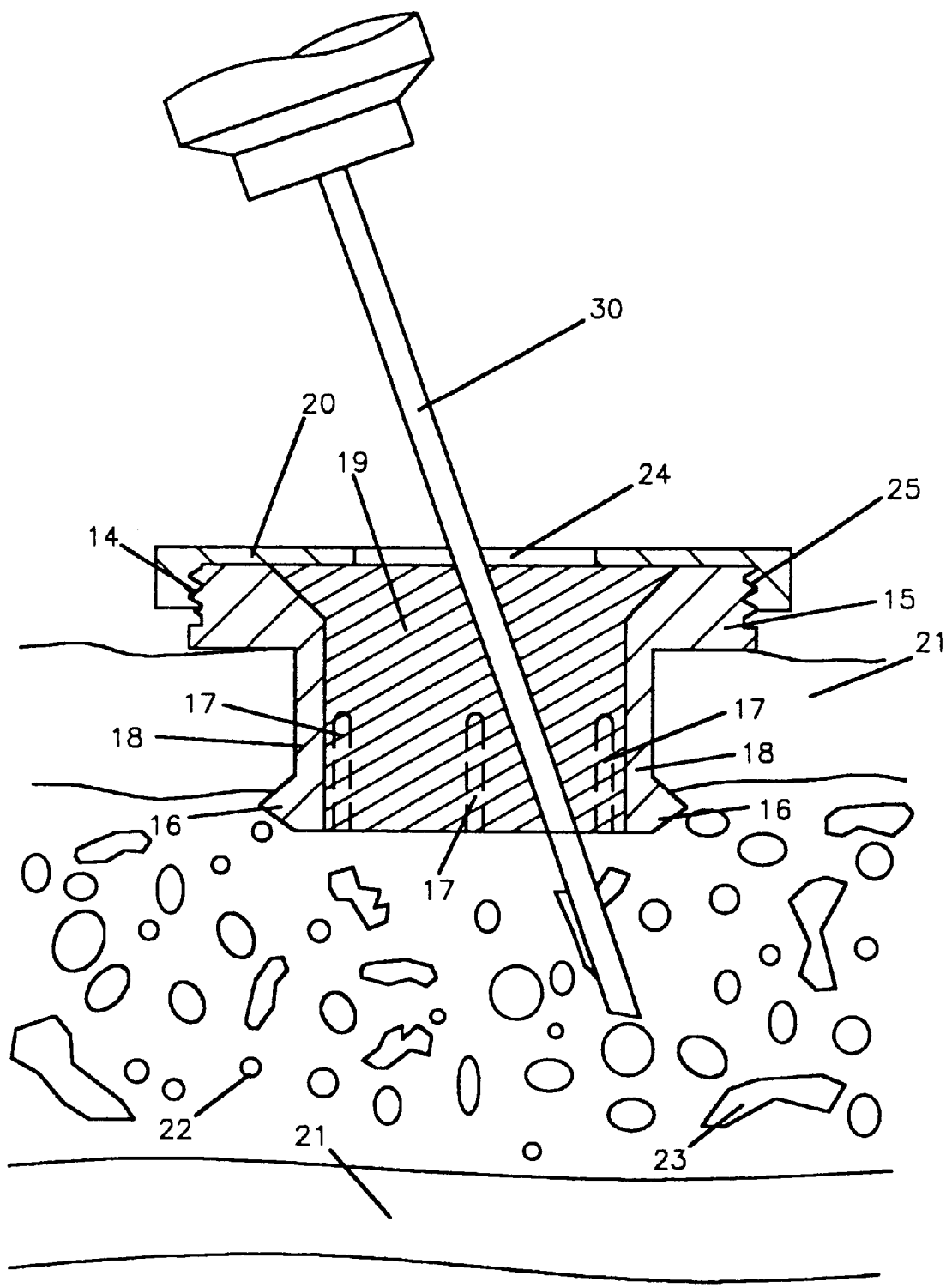
FIG. 5. is a cross-sectional plane view of an implant for infusion or aspiration in situ with port, penetrable seal insert, seal ring, cap and needle.

In another embodiment, a penetrable seal (19) may be used with a cap (20) having an insert access bore (24) and cap retaining threads (25) as shown in FIG. 2 and FIG. 5 for repeatable access into bone.

An advantage of the penetrable plug insert is the ability to remove and replace the plug without removing the access port and damaging surrounding cortical bone. Replacement of the plug may be needed when it is damaged by numerous needle insertions, for example.

In addition to a needle and a bone biopsy assembly, further instruments that may be used with the penetrable insert include any surgical instrument having a sufficiently sharp point so that it can puncture and be removed from the insert, such as a catheter, an endoscope, an infusion instrument, an aspiration instrument, a cutting tool, or the like.

Figure 4:
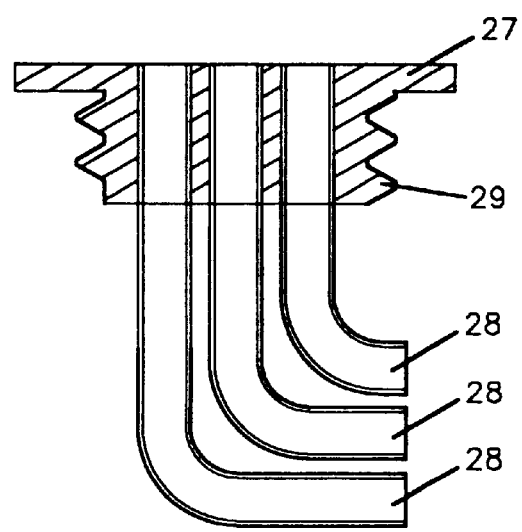
FIG. 4. is a cross-sectional plane view of an adapter insert with guide tubes for inserting instruments for aspiration, viewing or surgical manipulations, for example.
Figure 6:
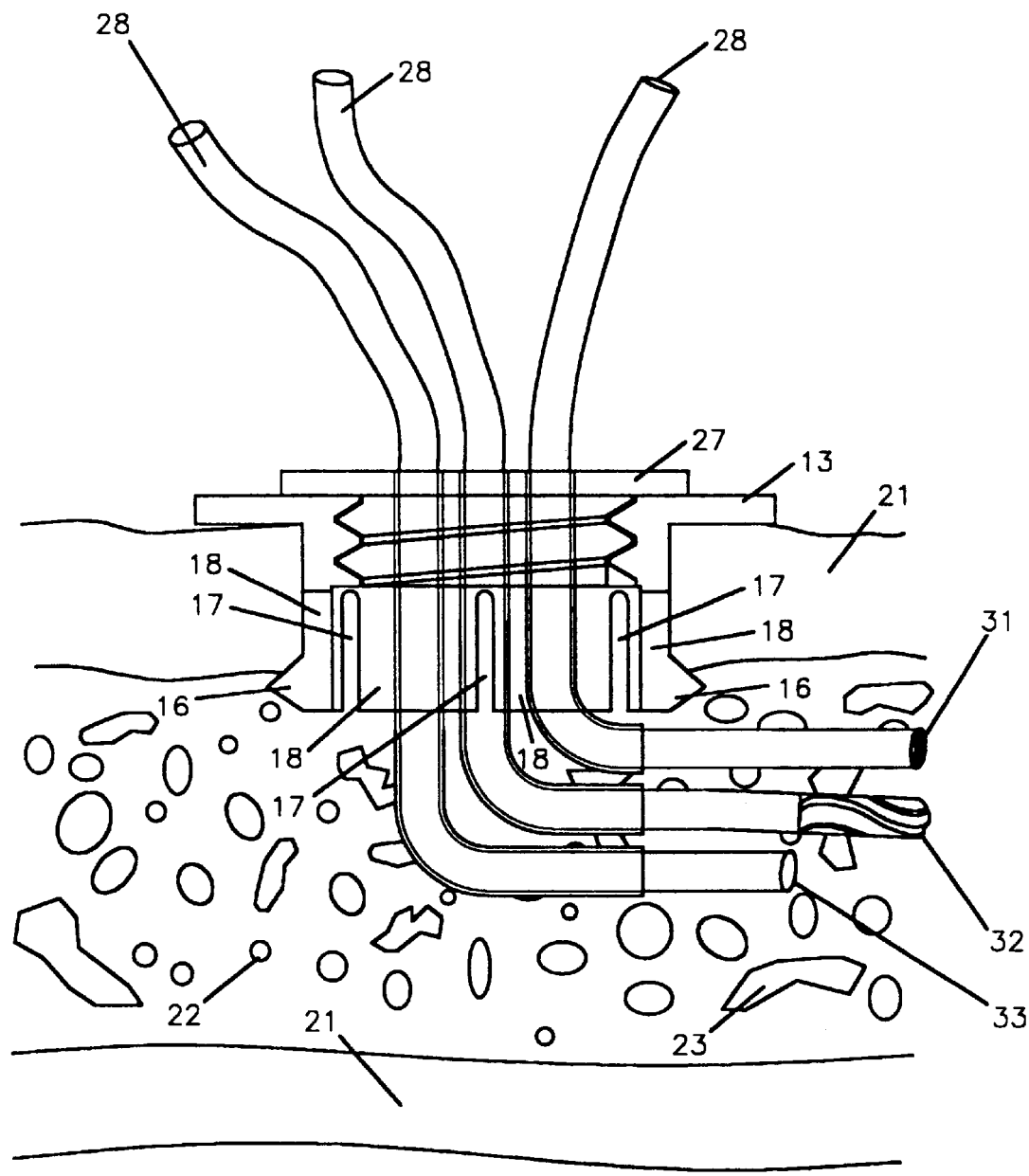
FIG. 6 is a cross-sectional plane view of an implant for bone access having an adapter insert with guide tubes for insertion of instruments for illumination, observation, aspiration, or cutting, for example, in situ in bone.

Adapter insert means: An alternative insert is an access port adapter insert (27). This adapter insert may be fitted with threads such that it fits into the bore (12) of either port (13) or port (15). An example of an insert fitted with threads (29), such that it fits with port (13), is shown in FIG. 4 and FIG. 6.

The adapter insert (27) may have one or a plurality of guide tubes (28) for facilitating use of surgically-related instruments for manipulation of bone, marrow, or cartilage. A guide tube (28) can be preshaped or formed from shape memory so that when it is subjected to body temperature, it returns to an original shape and guides an instrument down the long axis of the bone. Suitable materials for fabrication of a guide tube include. but are not limited to, shape memory alloys of nickel and titanium. A guide tube may be biocompatible tubing, a catheter, trocar or other cylindrical bone sampling instrument that could be used to restrict tissue encroachment into the bore and act as a guide or port into bone to facilitate the manipulation of surgical instruments. Pre-formed and rigid guide tubes may be made from a metal, polymer or a ceramic; the corresponding adapter insert (27) would be fabricated so as to fit with rigid guide tubes.

Examples of a surgically-related instrument include, but are not limited to, a fiber optic (31); a catheter (33); a bone biopsy assembly as described in U.S. Pat. No. 5.405,388; a cancellous access port system, an electrochemical measuring device, or a tissue containment device as described in Fox, WC, "Osseous Implants for Experimental Studies of Bone, Marrow, and Materials Biocompatibility," Dissertation, The University of Texas at Austin, May 1991; or a surgical instrument (32). Examples of a surgical instrument (32) include, but are not limited to, a knife, curette, rotating cutter (32), flexible shaft cutter, laser scalpel, electrical coagulator, suction instrument, clipper, or other mechanical, chemical, or sonic manipulator. A fiber optic (31) may be used for illumination, observation, cauterization, diagnosis, or surgical manipulation. A diagnostic application may measure intensity and wavelength of backscattered light to determine tissue health, for example. A catheter (33) may be used for infusion, or aspiration of body tissue or fluids.

Figure 7:
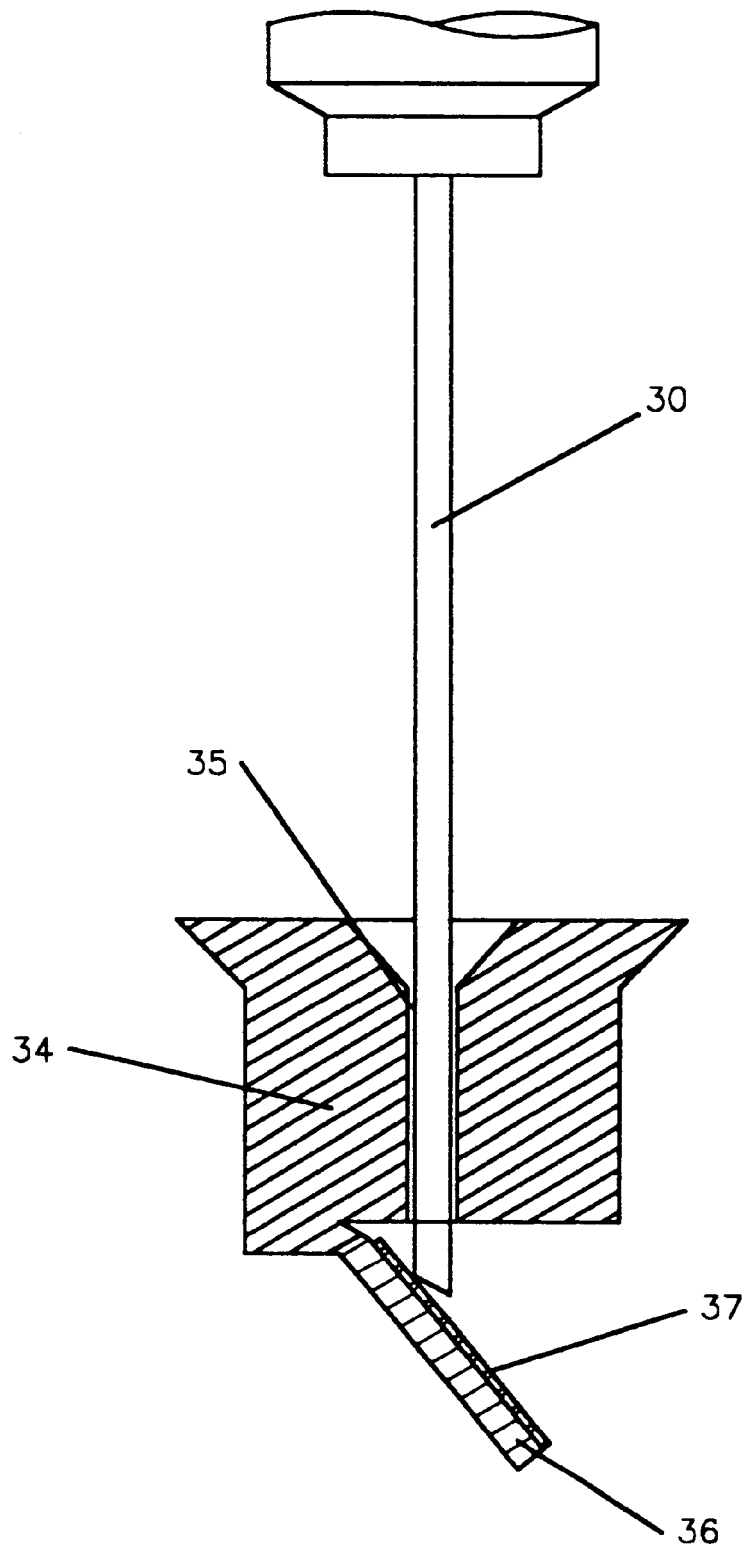
FIG. 7 is a cross-sectional plane view of an implant for bone access having an adapter insert with a needle guide port, a flapper strike plate, and a flapper valve for infusion or aspiration.

A further embodiment of an adapter insert is shown in FIG. 7 and is referred to as a needle flapper valve insert (34). This insert has a small port (35) that runs longitudinally through a central axis of the insert and a flapper valve (36). This insert guides a needle (30) through a needle guide port (35). The needle guide port (35) can seal following needle (30) withdrawal by closure of a strike plate (37). Alternatively, the needle guide port (35) is formed such that it is tapered, having a larger diameter at the end of needle (30) entry and a smaller diameter at the end of needle (30) exit. The small diameter should be sufficiently small such that elastic stress within adapter insert (34) causes closure of the needle guide port (35) following needle (30) removal. In the tapered embodiment, the small diameter end of the needle guide port (35) will open during the insertion of a needle (30) and close when the needle is withdrawn. These embodiments of the adapter insert having a tapered needle guide port (35) or a flapper strike plate (37) and flapper valve (36) have an advantage in that puncture-related mechanical degradation of an insert is minimized (FIG. 7).

A cap (20) or an adapter insert (27) may be contoured to minimize overlying soft-tissue irritation.

Figure 8:
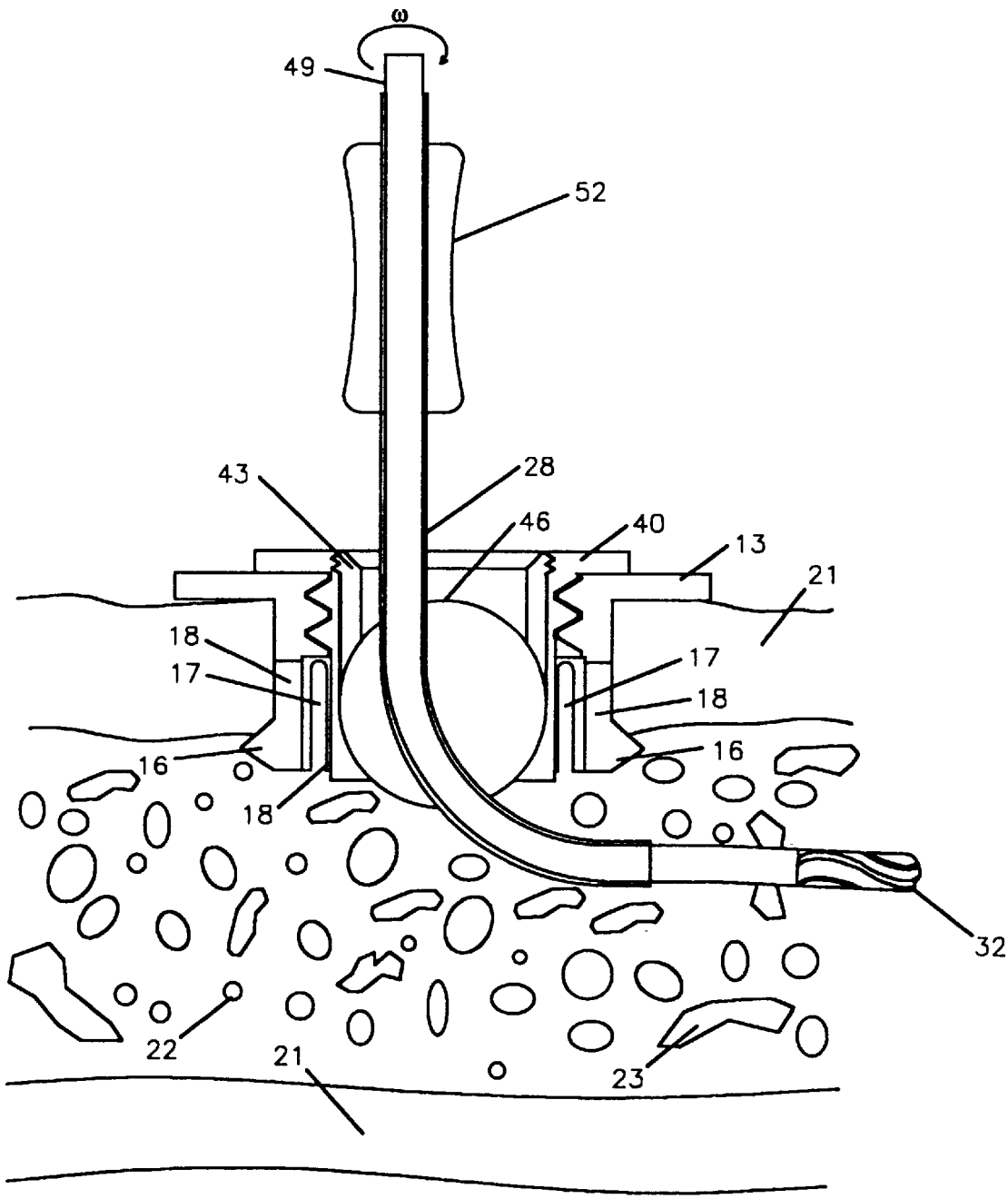
FIG. 8 is a cross-sectional plane view of an implant for bone access having an adapter insert fitted to a swivel ball, and a swivel ball, for guiding surgical instruments to distal sites for surgery.

Another embodiment of an adapter insert is shown in FIG. 8 and is referred to as a swivel ball adapter insert. This swivel ball adapter insert (40) fastens to the bore of port (13) or outer surface of port (15), is contoured to matchingly fit a swivel ball (46), has a bore at one end having a radius that reduces the bore diameter and forms a concave surface that matches the convex surface of the swivel ball (46), and includes a keeper ring (43) and a swivel ball (46). The swivel ball (46) is free to rotate within the swivel ball adapter insert (40) and has a bore for insertion of a guide tube (28), the bore being cylindrical, curved, square, or combinations thereof. More than one bore may be present in the swivel ball. When a guide tube (28) is inserted through the bore of a swivel ball (46), the guide tube enters bone through the end of the adapter insert (40) bore having the small diameter and concave surface. The embodiment may further include a surgical instrument such as a cutter having a drive shaft (49), and a grip (52) for manipulating the guide tube (28) and swivel ball (46). The use of a swivel ball (46) with a guide tube (28) allows a surgeon to direct an instrument such as a cutter (32) to distal sites of surgery. The swivel ball (46) allows 360 degrees of rotation about the longitudinal axis of the access port (13, 15) and at angles ranging from near zero to 90 degrees off axis with respect to the longitudinal axis of the access port (13, 15). When a guide tube (28) is not inserted through the swivel ball (46), the bore of the swivel ball may be filled with flexible wire, and the swivel ball (46) turned such that the bore no longer provides a channel into bone.

Uses and Procedures: The present implant port provides instrument access to the medullary compartment of bone, and a port into osseous structures. This implant port is useful for performing bone surgery such as cutting, cauterizing, or biopsying; for viewing bone and marrow tissue; for infusing materials to bone, such as percutaneous osseous infusion; for delivering fluids to the cardiovascular system; and for aspirating fluids from a patient.

For use of the implant port of the present invention, a cortical bone (21) orifice is constructed having a size about equal to the diameter of the access port (15, 13) but less than the combined diameter of the access port (15, 13) and bead (16). The orifice may be a threaded or a smooth drilled osseous orifice. The access port (15, 13) operates when placed in the orifice by mechanically locking to the internal surface of the hole. As the port (15, 13) is pushed into the hole, the bead (16) on the outer surface of the fluted end of the port forces the walls (prongs, 18) of the fluted end to strain towards the centrum of the port. This movement of the walls or prongs of the port (15, 13) is required because the outside diameter of the port (15, 13) in the area of the bead (16) is greater than the inside diameter of the hole in bone. This elastic strain or deforming action forces the bead (16) into the internal surface of the hole, causing the implant to resist forces which tend to push the port (15, 13) into bone or pull the port (15, 13) from the hole. In a bone with a thin cortex, the bead (16) may reach through the hole and expand outwardly, causing the bead (16) to partially reach beyond the backside of the hole, and cause the contour of the bead (16) to direct the elastically generated force in such a way that it pushes against the walls of the cortical bone (21) defect and downward on the port (15, 13), causing the port (15, 13) to further seal against the bone. Once the access port (15, 13) is fixed in cortical bone (21), a penetrable insert (19), or an adapter insert (27, 34, 40) is placed in the bore (12).

The implant port of the present invention maintains an opening through hard cortical bone (21) and allows manipulation of medullary tissue, including cancellous trabecular bone (23), marrow or bone cells (22), or cortical bone (21) from the inside. If an insert (27, 34, 40) is placed to allow bone surgery from the inside of bone to the outside, instruments are inserted through guide tubes (28) to perform surgical manipulation of bone, marrow or cartilage. Nonhealing fractures of long bone can be treated by implantation of the implant in healthy bone adjacent to the fracture which would allow manipulation of nonhealing tissue from the inside. This procedure protects overlying vascular supply, minimizes the potential for infection, reduces morbidity, and provides an opportunity to implant a bone scaffolding of osteogenetic substance or to apply locally a pharmaceutical or biologic agent to treat the injury. A local pharmaceutical agent may include, but is not limited to, an anti-cancer agent, analgesic, anti-inflammatory, or an antibiotic. A biologic agent may include, but is not limited to, transforming growth factor beta or alpha, bone morphogenic protein, fibroblast growth factor, tumor necrosis factor, nerve growth factor, or vascular permeability factor.

Once the implanting procedure is complete, and if further procedures are expected, the instruments are removed and flexible biocompatible wires may be inserted in the guide tubes (28) to keep tissue from forming within their inner diameter. The skin is closed over the device. The implant must be surgically accessed to perform further manipulations. If further procedures are not expected, the device is pulled from the site and skin is closed over the cortical bone (21) defect. If the penetrable insert (19) is used, skin can be left retracted or sutured closed for subsequent percutaneous access by needle (30).

If the implant port is used as a bone aspirate collection port, the aspirate can be collected, separated into vital wound healing components, and administered to the patient. Collection may be vacuum driven. Separation may include centrifugation and filtering. Administration may include the combination of the autologous tissue with donor or synthetic bone replacement material.

Additionally, if blockage of the bone occurs proximal or distal to the implant port, the insert (19, 27, 34, 40) can be removed and flexshaft driven cutters can be introduced to open the blockage and restore access to the cardiovascular system.

Figure 9:
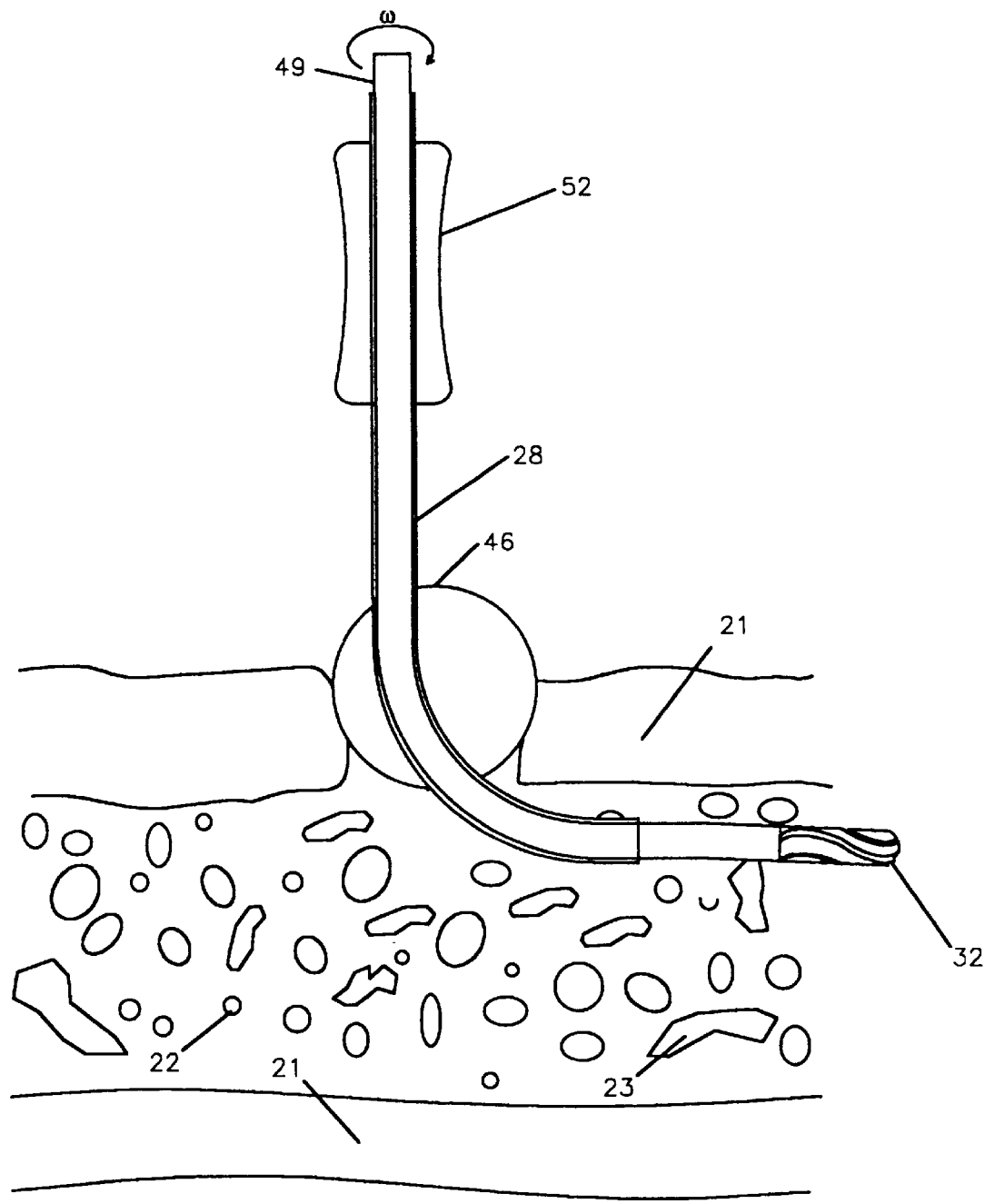
FIG. 9 is a cross-sectional plane view of a swivel insert assembly that may be used by itself or with an access port of the present invention.

Insert Assemblies and Uses Thereof: For temporary use, and for use where an assembly is held in place by an external means, such as by hand, the present invention contemplates the use of an insert assembly without the use of an access port as heretofore described. An insert assembly means an insert and one or more surgical instruments. In particular, a swivel ball insert assembly, as shown in FIG. 9, can be used for manipulation through a defect or surgically created orifice in bone. A swivel ball insert assembly may comprise a swivel ball (46), guide tube (28), and a surgical instrument such as a rotating cutter (32). In a further embodiment, an adapter insert (40) may be used with a swivel ball insert assembly. In a further embodiment, a swivel ball assembly may comprise a swivel ball (46), keeper ring (43), guide tube (28), and an adapter insert (40). A further insert assembly may comprise an adapter insert (27) and guide tube (28).

Use of an insert assembly without an access port has an advantage in that a uniform orifice in bone is not required. Disadvantages include i) hemorrhage is not stopped around the device, ii) the assembly must be held in place continuously when in use, and iii) the assembly does not have rigid fixation to bone so as to provide accurate manipulation of an instrument.

In situations where an irregular defect in bone exists, or where little bone manipulation is required, a guide tube (28) can be used alone to guide instruments into the medullary compartment of bone. The performance and ease of use of the guide tube can be enhanced by use of a swivel ball (46) with or without an adapter insert (40) and keeper ring (43). These embodiments have disadvantages compared with use of the implant port of the present invention, but in some patient situations, may be more desirable.

EXAMPLE 1

Implant Port Implanted in Tibia of Rabbits

An access port (13) has been placed in the tibial metaphysis of four New Zealand White Rabbits bilaterally. The eight access ports were easily placed into a surgically constructed orifice in the tibia by manually pushing the port into the orifice. The elastic prongs strained to allow the implant to be placed and, once placed, the access port was held tightly by pressure from the prongs on the orifice. An adapter insert (27) with guide tube (28) and, subsequently after manipulation, a penetrable insert (19) was placed into the access port. An adapter insert, together with a rotating cutter (32), and catheter having combined infusion and aspiration bores were introduced into the medullary compartment of the tibia near the knee and manipulated so as to reach sites as distant as the distal metaphysis of the tibia just above the ankle.

Manipulations have been performed throughout the medullary compartment of a tibia of one study animal. Subsequently, adapter inserts were removed and penetrable inserts (19) were positioned in the access port and used for repeated percutaneous infusion. Infusion pressures and rates were measured. Infusion pressure associated with the medullary compartment ranges between 20 and 30 mm Hg. Infusion rates can reach over one liter per hour. Following more than 200 injections into one of the penetrable inserts (19), the insert (19) was replaced and the implant site was again used for percutaneous osseous infusion.

EXAMPLE 2

Therapeutic Delivery of Bone Matrix Material and Growth Factors

In further studies in a baboon and a rabbit using an implant (access port (13) and adapter insert 27) of the present invention, bone tissue and growth factors were placed into the medullary compartment of bone to effect bone healing. Bone matrix and marrow aspirate from a second site in the same animal was infused through a catheter using the adapter insert (27) to provide a therapeutic scaffolding to support conduction of bone across a defect. Growth factors in the marrow aspirate were infused through the port using an infusion catheter and their effect on distal sites were evaluated. These studies involving tissue implantation using an instrument placed in the bore of the port (13) have demonstrated the use of this invention for therapeutic delivery of tissue.

EXAMPLE 3

Use of Insert Assemblies Without Access Port

In separate studies, a guide tube (28) with adapter insert (27) together with a rotating cutter (32) and catheter with combined infusion and aspiration bores were introduced into the tibia without the use of the port (13). These instruments were used to manipulate medullary bone, aspirate marrow tissue and infuse saline. Control of the instruments was not as precise as with the system of Example 2 and a poor seal between the adapter insert (27) and bone allowed excessive and problematic hemorrhage.

All of the devices and methods disclosed and claimed herein can be made and executed without undue experimentation in light of the present disclosure. While the devices and methods of this invention have been described in terms of preferred embodiments, it will be apparent to those of skill in the art that variations may be applied to the device, methods and in the steps or in the sequence of steps of the method described herein without departing from the concept, spirit and scope of the invention. All similar substitutes and modifications apparent to those skilled in the art are deemed to be within the spirit, scope and concept of the invention as defined by the appended claims.

I claim:

1. A surgical instrument port system for access to a medullary compartment of bone or cartilage and for manipulation of bone or marrow, said system comprising:
    a port having an outer surface and an inner surface, the inner surface formed by a longitudinally oriented bore, a predetermined length terminating in a first end and a second end, a plurality of longitudinally oriented flutes that penetrate the outer surface and extend from the first end for a significant portion of the port length, the flutes allowing the first end to deform for insertion into bone or cartilage, at least one bead on the outer surface adjacent to the first end, the bead locking the port in bone or cartilage when in use;
    an insert adapted to fit into the bore of the port, the insert having an insert bore contoured to matchingly fit a swivel ball; and
    a swivel ball having a bore therethrough for insertion of a surgically-related instrument, the insert and swivel ball substantially filling the bore of the port when positioned in the port.

2. The system of claim 1 in combination with a guide tube inserted through the bore of the swivel ball for guiding a surgically-related instrument, the guide tube having a guide tube bore.

3. The system of claim 2 in combination with a surgically-related instrument positioned within the guide tube bore.

4. The system of claim 3 wherein the surgically-related instrument is selected from the group consisting of an optical device, a manually driven cutter, a motor driven cutter, a suction instrument, a catheter, a needle, a knife, a curette, a clipper, a laser scalpel, an electrical coagulator, a mechanical manipulator, a chemical manipulator, and a sonic manipulator.

5. The system of claim 2 wherein said guide tube is selected from the group consisting of a catheter and a trocar.

6. The system of claim 2 in combination with a biocompatible wire inserted into the guide tube bore for preventing tissue formation within said guide tube.

7. A bone insert system for access to the medullary compartment of bone, consisting essentially of:
    an insert selected from the group consisting of
        i) a swivel ball having a bore therethrough, and
        ii) an insert having a bore, the insert bore contoured to matchingly fit a swivel ball, the insert in combination with a swivel ball having a bore therethrough, and
    a surgically related instrument positioned within the insert bore wherein, when in use, said system is unattached to bone cortex and is freely movable relative to bone cortex.

8. The bone insert system of claim 7 wherein the insert is an insert having a bore, the insert bore contoured to matchingly fit a swivel ball, the insert in combination with a swivel ball having a bore therethrough.

9. The bone insert system of claim 7 in combination with a guide tube positioned within the insert bore, the guide tube having a bore therethrough.

10. The bone insert system of claim 7 wherein the surgically related instrument is selected from the group consisting of a rotating cutter and an optical device.

11. The bone insert system of claim 7 wherein the insert is a swivel ball having a bore therethrough and a guide tube positioned within the swivel ball bore.

12. The bone insert system of claim 8 wherein the swivel ball is in combination with a guide tube positioned within the swivel ball bore.

13. The bone insert system of claim 7 wherein the insert is an insert having a bore, the insert in combination with a guide tube, the guide tube positioned within the insert bore.

14. The bone insert system of claim 12 wherein the guide tube is a catheter and the surgically related instrument is a rotating cutter.

15. A bone insert system for access to the medullary compartment of bone, consisting essentially of:
    a swivel ball having a bore therethrough;
    a guide tube positioned within the swivel ball bore, the guide tube having a guide tube bore therethrough; and
    a surgically-related instrument positioned within the guide tube bore wherein, when in use, the system is unattached to bone cortex and freely movable relative to bone cortex.

16. A method of performing surgery of bone comprising positioning the system of claim 3 in bone or cartilage; and performing surgery of bone or cartilage.

17. The method of claim 16 wherein positioning of the implant occurs at a first site in bone or cartilage, and surgery of bone is at a second site of the bone or cartilage from within bone using the surgically related instrument positioned at the first site.

18. A method of performing surgery of bone comprising positioning the bone insert system of claim 7 in bone cortex for access to the medullary compartment of bone; and performing surgery of bone.

19. The method of claim 18 wherein positioning of the implant occurs at a first site in bone or cartilage, and surgery of bone is at a second site of the bone or cartilage from within bone using the surgically related instrument positioned at the first site.

20. A method of performing surgery of bone comprising positioning the bone insert system of claim 15 in bone cortex for access to the medullary compartment of bone; and performing surgery of bone.

21. The method of claim 20 wherein positioning of the implant occurs at a first site in bone or cartilage, and surgery of bone is at a second site of the bone or cartilage from within bone using the surgically related instrument positioned at the first site.

* * * * *